United States Patent [19]

Margolis

[11] Patent Number: 5,070,108

[45] Date of Patent: Dec. 3, 1991

[54] METHODS OF TREATING OSTEOPOROSIS, INCREASING BONE MINERAL CONTENT AND PREVENTING THE OCCURRENCE OF COMPRESSION FRACTURES IN A MAMMAL

[75] Inventor: David J. Margolis, Philadelphia, Pa.

[73] Assignee: Trustees of the University of Pennsylvania, Philadelphia, Pa.

[21] Appl. No.: 596,676

[22] Filed: Oct. 12, 1990

[51] Int. Cl.[5] .............................................. A61K 31/07
[52] U.S. Cl. ................................................... 514/725
[58] Field of Search ......................................... 514/725

[56] References Cited

U.S. PATENT DOCUMENTS

| | | | |
|---|---|---|---|
| 3,746,730 | 7/1973 | Marbet et al. | 260/413 |
| 3,931,257 | 1/1976 | Pawson | 260/408 |
| 3,950,418 | 4/1976 | Bollag et al. | 260/557 |
| 4,054,589 | 10/1977 | Bollag et al. | 260/408 |
| 4,061,656 | 12/1977 | Klaus et al. | 260/332.2 A |
| 4,105,681 | 8/1978 | Bollag et al. | 260/404 |
| 4,889,847 | 12/1989 | Kligman et al. | 514/171 |

*Primary Examiner*—Stanley J. Friedman
*Attorney, Agent, or Firm*—Woodcock Washburn Kurtz Mackiewicz & Norris

[57] ABSTRACT

Methods of treating osteoporosis, increasing bone mineral content and preventing the occurrence of compression fractures are provided comprising administering to a mammal in need of such treatment a retinoid such as etretinate.

17 Claims, No Drawings

METHODS OF TREATING OSTEOPOROSIS, INCREASING BONE MINERAL CONTENT AND PREVENTING THE OCCURRENCE OF COMPRESSION FRACTURES IN A MAMMAL

FIELD OF THE INVENTION

This invention relates to a method of treating osteoporosis. More particularly, methods of treating osteoporosis, increasing bone mineral content and preventing the occurrence of compression fractures with retinoids are provided.

BACKGROUND OF THE INVENTION

Osteoporosis is considered to be one of the most debilitating diseases of the adult population in the industrialized nations. Osteoporosis is the general term used for diseases of diverse etiology that are characterized by a reduction in the mass of bone per unit volume to a level below that required for adequate mechanical support (Krane, S. M., et al., "Metabolic Bone Disease," in *Harrison's Principles of Internal Medicine,* pg. 1889 edition 11 (1987)). One form of osteoporosis is senile osteoporosis which is responsible for a large portion of the health dollars spent on the geriatric population (Resnick, N. M., et al., "Senile Osteoporosis Reconsidered," *JAMA* 261:1025-1029 (1989)). The two other most common forms of osteoporosis are peri- or postmenopausal osteoporosis and corticosteroid induced osteoporosis. The most devastating consequence of osteoporosis is the occurrence of a pathologic fracture in trabecular bone, such as the vertebral spine or the hip. No current medical regimen is effective in fully preventing this common malady and no treatments are capable of reversing this affliction.

The pathophysiology of osteoporosis is poorly understood. It probably is related to an interplay of osteoblasts, osteoclasts, and other hormonally mediated events that alter calcium homeostasis. Most current treatment strategies attempt to reduce the bone loss of calcium in order to retard the onset of osteoporosis (Dawon-Hughes, B. et al., "A controlled trial of the effect of calcium supplementation on bone density in postmenopausal women," *NEJM* 323:878-83 (1990)); Storm, T. et al., "Effect of intermittent cyclical etidronate therapy on bone mass and fracture rate in women with postmenopausal osteoporosis," *NEJM* 322:1264-1271 (1990)). Attempts to produce new and structurally functional bone have not been successful (Riggs, B. L. et al., "Effect of fluoride treatment on the fracture rate in postmenopausal women with osteoporosis," *NEJM* 322:802-809 (1990)).

Retinoids are currently approved by the FDA for use in the treatment of cystic acne and psoriasis vulgaris. However, they have also been used in the treatment of Darier's disease, pityriasis ruba pilaris, and basal cell nevus syndrome (Ellis, C. N. et al., "Etretinate therapy," *JAAD* 16:267-291 (1987); Leyden J. J. "Retinoid and acne," *JAAD* 19:267-291 (1988)). Bone discomfort occurs in a significant number of patients receiving these medications. Studies have demonstrated that ligaments and tendons of patients receiving retinoids may become calcified but that the bones of some of these patients may demonstrate osteopenia or the radiographic appearance that the bones are losing calcium (McGuire J. et al., "Skeletal changes associated with chronic isotretinoin and etretinate administration," *Dermatologica* 173:169-181 (1987)). The first study that has attempt to demonstrate an alteration in bone mineralization in patients on retinoids was unable to demonstrate any change in the bone mineral content in long bones (Torok, L. et al., "Bone scintigraphic examinations in patients treated with retinoid a prospective study," *Br J Derm* 120:31-36 (1989)). Animal studies have demonstrated that retinoids stimulate the bone remodeling cells (Teelman, K., "Retinoids toxicology and teratogenicity to date," *Pharmac Ther* 40:29-43 (1989)). Studies on osteoclasts have also demonstrated that retinoids appear to stimulate cellular activity (Trechsel U. et al., "Hypocalcemia induced with an arotinoid in thyroparathyroidectomized rats," *J Clin Invest* 80:1679-1686 (1987)).

Descriptions of the effects of retinoids, which are synthetic analogues of vitamin A, on bone have been confusing. Studies have noted calcification of ligaments and tendons, vertebral hyperostosis, periosteal thickening, and osteopenia (Melnick, B. et al., "Retrospective radiographic study of skeletal changes after long-term tretinate therapy," *Br J. Dermatol* 116:207-212 (1987); McGuire J., et al., "Skeletal changes associated with chronic isotretinoin and etretinate administration," *Dermatol* 175:169-81 (1987); Torok L. et al. "Bone-scintigraphic examinations in patients treated with retinoids: a prospective study," *Br J Dermatol* 120:31-36 (1989)). Studies have shown that retinoids can cause the synthesis of cellular products from cells of similar embryonic origin as bone forming cells (Ellis, C. et al., "Sustained improvement with prolonged topical tretinoin (retinoic acid) for photoaged skin," F. Supp. *JAAD* 23:629-637 (1990)).

Surprisingly in view of the literature on retinoids described herein, it has been demonstrated by the Applicant that retinoids can reverse the bone mineral loss that occurs in mammals with osteoporosis. It has also been observed that the gain in bone mineral loss appears to be functionally sound and prevents the occurrence of pathologic fractures.

SUMMARY OF THE INVENTION

There is provided by this invention a novel method for the treatment of osteoporosis comprising administering to a mammal, e.g. a human, in need of such treatment a retinoid, such as etretinate, or a pharmaceutically acceptable salt thereof in an amount effective for treating said osteoporosis.

Further provided by this invention is a novel method of increasing bone mineral content comprising administering to a mammal in need of such treatment a retinoid or a pharmaceutically acceptable salt thereof in an amount effective for increasing said bone mineral content.

Further provided by this invention is a novel method of preventing the occurrence of compression fractures due to osteoporosis comprising administering to a mammal in need of such treatment a retinoid or pharmaceutically acceptable salt thereof in an amount effective for preventing said compression fractures due to osteoporosis.

The Applicant has recognized that the use of retinoids in the treatment of osteoporosis would not only reduce the incidence of osteoporosis and increase the mineral content in bone, but as a result would decrease the number of bone fractures due to osteoporosis.

DETAILED DESCRIPTION OF THE INVENTION

As used herein, the term "retinoids" denotes vitamin A in its naturally occurring forms such as retinol, retinal, retinyl esters, retinoic acid as well as synthetic analogs of vitamin A. The ring on the analogs may be aromatic or heteroaromatic and the side chain may be optionally substituted with a halide such as chloride. The terminal group may be oxidized, reduced, esterified, etc. The alkali metal (sodium, potassium, etc.) and alkaline earth metal (magnesium, calcium, etc.) salts of a retinoid carboxylic acid are also included herein.

Examples of retinoids included within the present invention are vitamin A acid (hereinafter "isotretinoin") and 9-(4-methoxy-2,3,6-trimethylphenyl)-3,7-dimethyl-2,4,6,8-nonatetraenoic acid ethyl ester (hereinafter referred to as "etretinate").

These compounds and methods for their preparation are known. See e.g., U.S. Pat. No. 3,746,730, U.S. Pat. No. 3,931,257, U.S. Pat. No. 3,950,418, U.S. Pat. No. 4,054,589, U.S. Pat. No. 4,061,656, U.S. Pat. No. 4,105,681 and U.S. Pat. No. 4,889,847, which patents are incorporated by reference as if fully set forth herein.

The dosages in which the retinoids are administered can be varied according to the mode and route of administration and according to the requirements of the patient. For example, the dosage can be varied and lowered, if necessary, to avoid potential side effects such as loss of hair or cheilitis. The effective dose of retinoids and duration of treatment with retinoids by the methods of this invention are dependent on the age, weight, and condition of the patient. It is the concept of this invention that the effective dose of retinoid will help to prevent and reverse osteoporosis and prevent the occurrence of compression fractures. Advantageously, the retinoids used in the methods of the present invention are expected to be administered to mammals in need of such treatment at less than the dose currently being used for the dermatological condition the retinoid is indicated for. A daily dose of about 0.25 to about 2 mg of retinoid per kg of body weight and preferably at about 0.5 to about 1 mg of retinoid per kg body weight is expected to be useful. The compositions can be administered to the patient as a single dose or divided over several part doses. The compositions for use herein are very conveniently administered to mammals by any route of administration suitable for retinoids, e.g. oral, or parenteral. Preferably the retinoid is formulated with any suitable nontoxic pharmaceutically acceptable inert carrier material. Such carrier materials are well known to those skilled in the art of pharmaceutical formulations. For those not skilled in the art, reference is made to the text entitled *Remington's Pharmaceutical Sciences*, 17th edition, 1985, ed. Alfonso R. Gennaro, Mack Publishing Company, Easton, Pa. 18042. In a typical preparation for oral administration, e.g. tablet, capsule or caplet, the retinoid in an effective amount is combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac and/or sugar.

EXAMPLE 1

Patients in this example were females of non child bearing potential receiving retinoids for severe dermatologic diseases. All five patients had received the retinoid etretinate for at least 4 months at doses in the range from 25 to 50 mg per day. The dose range of retinoid was determined by their skin disease. Their skin disease is not known to be associated with their osteoporosis, although these patients may have received corticosteroids in the past which are associated with osteoporosis. Bone mineralization was determined by Dual-photon absorptiometry (DPA) of the lumbar spine. Readings that were influenced by calcium deposits that are not part of the lumbar spine were disregarded. All patients were compared to an established group of age matched controls.

Five patients were studied and all patients demonstrated an increase in the bone mineral content of their lumbar spine as compared to age matched controls (Table 1). None of the patients had a bone mineralization of less than the age matched control subjects. On average the group demonstrated DPA values that were 114% of control. There was a trend toward higher values in patients whom had received the retinoid for a longer period of time.

The most revealing patient was an 85 year old woman with a history of several pathologic compression fractures of her vertebral spine. Her osteoporosis was believed to be secondary to a several year history of systemic glucocorticoid administration (glucocorticoid induced osteoporosis) and advanced age (senile osteoporosis). She had received retinoid therapy (etretinate at about 25 to 50 mg per day) for approximately one year when she was studied. At time of evaluation for this Example, she had no radiographic evidence of additional compression fractures of her vertebral spine. The DPA examination revealed that her lumbar spine had 111% of the bone mineral content of age matched controls. More impressively, when her DPA examination was compared to a control population with an equivalent number of vertebral compression fractures, she had 182% of the expected bone mineral content. During a follow-up period of 6 months she still shows no radiographic evidence for additional compression fractures of her vertebral spine. The natural history of such a patient is to have 1 to 3 vertebral compression fractures per year (Riggs, et al. "Effect of fluoride treatment on the fracture rate in postmenopausal women with osteoporosis," *NEJM* 322:802–9 (1990)) and she has had approximately 18 months without a fracture. The patient had continued on etretinate intermittently at a dose of about 25 mg to 50 mg per day throughout the 18 month follow up.

TABLE 1

| Summary of Clinical Data | | | | | |
| --- | --- | --- | --- | --- | --- |
|  | #1 | #2 | #3 | #4 | #5 |
| Age | 85 | 73 | 52 | 41 | 53 |
| Sex | F | F | F | F | F |
| BMD | 1.02 | 1.09 | 1.25 | 1.58 | 1.22 |
| % ctl~ | 111 | 118 | 115 | 118 | 108 |

*BMD—Bone mineral density in grams/centimeters squared
~% ctl—Percentage expected of age matched control The patients in this example clearly demonstrate that women receiving retinoids have an increase in their bone mineralization as compared to age matched controls. It also appears that this increase in bone formation is functional bone that is not predisposed to fracture. Therefore this increase in bone formation appears to reverse osteoporosis.

I claim:

1. A method of treating osteoporosis comprising administering to a mammal in need of such treatment a retinoid or a pharmaceutically acceptable salt thereof in an amount effective for treating said osteoporosis.

2. The method of claim 1 wherein the mammal is a human.

3. The method of claim 1 wherein the retinoid is etretinate.

4. The method of claim 1 wherein the osteoporosis is senile osteoporosis.

5. The method of claim 1 wherein the retinoid is administered orally.

6. A method of increasing bone mineral content comprising administering to a mammal in need of such treatment a retinoid or a pharmaceutically acceptable salt thereof in an amount effective for increasing said bone mineral content.

7. The method of claim 6 wherein the mammal is a human.

8. The method of claim 6 wherein the retinoid is etretinate.

9. The method of claim 6 wherein the retinoid is administered orally.

10. The method of claim 6 wherein the bone is trabecular bone.

11. The method of claim 6 wherein the mammal in need o such treatment has osteoporosis.

12. The method of claim 11 wherein the osteoporosis is senile osteoporosis.

13. A method of preventing the occurrence of compression fractures due to osteoporosis comprising administering to a mammal in need of such treatment a retinoid or pharmaceutically acceptable salt thereof in an amount effective for preventing said compression fractures due to osteoporosis.

14. The method of claim 13 wherein the mammal is human.

15. The method of claim 13 wherein the retinoid is etretinate.

16. The method of claim 13 wherein the osteoporosis is senile osteoporosis.

17. The method of claim 13 wherein the retinoid is administered orally.

* * * * *